United States Patent
Straker

(10) Patent No.: US 10,912,807 B1
(45) Date of Patent: Feb. 9, 2021

(54) METHODS FOR PREPARING FULL SPECTRUM CANNABIS ELIXIR

(71) Applicant: Sheldon I.B. Straker, Fall River, MA (US)

(72) Inventor: Sheldon I.B. Straker, Fall River, MA (US)

(*) Notice: Subject to any disclaimer, the term of this patent is extended or adjusted under 35 U.S.C. 154(b) by 0 days.

(21) Appl. No.: 16/659,411

(22) Filed: Oct. 21, 2019

(51) Int. Cl.
| | |
|---|---|
| *A61K 36/00* | (2006.01) |
| *A61K 36/185* | (2006.01) |
| *A61K 47/44* | (2017.01) |
| *A61K 31/352* | (2006.01) |
| *A61K 9/00* | (2006.01) |
| *A61K 9/48* | (2006.01) |

(52) U.S. Cl.
CPC .......... *A61K 36/185* (2013.01); *A61K 9/0014* (2013.01); *A61K 9/0053* (2013.01); *A61K 9/48* (2013.01); *A61K 31/352* (2013.01); *A61K 47/44* (2013.01); *A61K 2236/15* (2013.01); *A61K 2236/33* (2013.01); *A61K 2236/37* (2013.01)

(58) Field of Classification Search
CPC ...................................... A61K 36/00
USPC .......................................................... 424/725
See application file for complete search history.

(56) References Cited

FOREIGN PATENT DOCUMENTS

CN 106518377 * 3/2017

\* cited by examiner

*Primary Examiner* — Michael V Meller

(57) ABSTRACT

Method for preparing full spectrum cannabis elixir is disclosed. The method comprises steps of breaking cannabis buds into small pieces to form an organic mixture and placing this organic mixture in an oven safe container. The container may be placed in an oven for decarboxylating the organic mixture. The decarboxylated mixture may be mixed and shaken with cold high proof grain alcohol to form an intermediate. Alternatively, the decarboxylated mixture and alcohol is mixed in magical butter or mighty fast herbal infuser to form an intermediate. This intermediate may be filtered using a press or coffee filter. Alcohol content may be removed from this filtered mixture using solvent extractor and water bath. This extract is mixed with organic cold pressed extra virgin coconut oil and lecithin liquid. Lastly, organic cold pressed unrefined hemp seed oil is added and stirred thoroughly to form a full spectrum cannabis extract (Keira's Elixir).

1 Claim, No Drawings

METHODS FOR PREPARING FULL SPECTRUM CANNABIS ELIXIR

BACKGROUND

*Cannabis* extracts are being increasingly used for their medicinal properties around the world. Extracts such as oils, elixirs, and the like have anti-inflammatory properties. Tetrahydrocannabinol (THC) is one of at least 113 cannabinoids identified in cannabis. THC is the principal psychoactive constituent of cannabis. With chemical name tetrahydrocannabinol, the term THC also refers to cannabinoid isomers.

In the *Cannabis* plant, THC occurs mainly as tetrahydrocannabinolic acid (THCA, 2-COOH-THC, THC-COOH). Geranyl pyrophosphate and olivetolic acid react, catalysed by an enzyme to produce cannabigerolic acid, which is cyclized by the enzyme THC acid synthase to give THCA. Over time, or when heated, THCA is decarboxylated, producing THC. While THC is generally well known for its intoxicating properties, the plant has a wealth of tetrahydrocannabinolic acid (THCA), a non-psychoactive compound found within the trichomes of living cannabis plants.

THCA is believed to offer an assortment of medicinal benefits, and is commonly used as a nutritional supplement and dietary enhancement for its:

Anti-inflammatory properties: A 2011 study (Evaluation of the Cyclooxygenase Inhibiting Effects of Six Major Cannabinoids Isolated from *Cannabis sativa*, available at: https://www.jstage.jst.go.jp/article/bpb/34/5/34_5_774/_article) published in the Biological and Pharmaceutical Bulletin suggested that, along with other cannabinoids, THCA demonstrated anti-inflammatory properties.

Anti-proliferative properties: A 2013 study that analyzed cell cultures and animal models concluded that THCA could prevent the spread of prostate cancer cells.

Neuroprotective properties: In a 2012 preclinical study (Effects of cannabinoids Δ(9)-tetrahydrocannabinol, Δ(9)-tetrahydrocannabinolic acid and cannabidiol in MPP+ affected murine mesencephalic cultures, available at: https://www.ncbi.nlm.nih.gov/pubmed/22571976) published in Phytomedicine, researchers found that THCA showed the ability to help protect against neurodegenerative diseases.

Antiemetic properties (increasing appetite and decreasing nausea)—A 2013 study (Tetrahydrocannabinolic acid reduces nausea-induced conditioned gaping in rats and vomiting in *Suncus murinus*, available at: https://bpspubs.onlinelibrary.wiley.com/doi/full/10.1111/bph.12316) conducted by researchers at the University of Guelph in Ontario found that both THCA and CBDA were effective in reducing nausea and vomiting in rat models, even more so than THC and CBD, respectively.

Hence, it will be beneficial to develop a process for creating a full spectrum cannabis elixir.

DETAILED DESCRIPTION

In the following description of the embodiments of the invention, reference is made to show by way of illustration specific embodiments in which the invention may be practiced. These embodiments are described in sufficient detail to enable those skilled in the art to practice the invention, and it is to be understood that other embodiments may be utilized and that changes may be made without departing from the scope of the present invention. The following detailed description is, therefore, not to be taken in a limited sense, and the scope of the present invention is defined only by the appended claims.

The specification may refer to "an", "one" or "some" embodiment(s) in several locations. This does not necessarily imply that each such reference is to the same embodiment(s), or that the feature only applies to a single embodiment. A single feature of different embodiments may also be combined to provide other embodiments.

As used herein, the singular forms "a", "an" and "the" are intended to include the plural forms as well unless expressly stated otherwise. It will be further understood that the terms "includes", "comprises", "including" and/or "comprising" when used in this specification, specify the presence of stated features, integers, steps, operations, elements and/or components, but do not preclude the presence or addition of one or more other features integers, steps, operations, elements, components, and/or groups thereof. As used herein, the term "and/or" includes any and all combinations and arrangements of one or more of the associated listed items.

Unless otherwise defined, all terms (including technical and scientific terms) used herein have the same meaning as commonly understood by one of ordinary skill in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terms "cannabis flower", "cannabis", "cannabis buds", and "cannabis plant" may be used interchangeably throughout this document. The usage is merely for the purpose of reference based on the context of each sentence and may not limit the scope of the present disclosure in any manner. The unit fluid ounce may be denoted by "fl. oz", "fl oz", or "fl. oz." representing the unit of volume.

Methods for preparing Keira's elixir—a full spectrum cannabis elixir is disclosed. The approach disclosed herein may provide regular strength Keira's Elixir which may be encapsulated, bottled for topical or oral application, or bottled in roller bottles for topical application.

The method disclosed herein is an extraction process made with a uniquely fortuitous process that may allow for a full spectrum cannabis extraction. The elixir may also be made using hemp flower to create a CBD infused or CBD sole formulation that may still be full spectrum minus the effects of higher THC content cannabis.

The resulting elixir may contain the cannabinoid profile of the original plant which includes the constituent terpenes i.e., the resulting elixir may have the same effects as the constituent strain from which it is extracted. The ratios of cannabinoids in the activated state and inactivated state can be specifically scaled to a desired end while preparing the elixir using the techniques mentioned herein.

For instance, a 2:1 active to inactive state formulation may be formulated thereby having the elixir deliver controlled and desired effects of each state. This ratio allows for both symptom relief as well as relief from the underlying cause, which may typically be inflammation. The raw materials needed may usually be the unsellable parts of the plant such as trim, kief, small nuggets, and/or the portions that fall off during storage and preparation of cannabis and hemp flower (shake).

The ingredients for preparing the elixir may include organic cannabis (buds or shake, shake may yield a more powerful elixir as it typically has more resin per oz), organic cold pressed unrefined hemp seed oil, organic cold pressed extra virgin coconut oil, organic lecithin liquid, and grain alcohol (190 proof/95% ethanol).

The equipment required for practicing the method may include Source Turbo Herbal Extractor (or similar extractors), Mighty Fast Herbal Infuser (or similar infusers), Single-Channel Pipettor Adjustable Micro Pipette (1-10 ml), 000 Capsule holder/filler, 000 capsule blanks, 1 oz dropper bottles, measuring cups, coffee filter, potato press, funnels, Mason jars (12 oz and/or 24 oz), hot water bath, gloves, and a freezer.

The first step of the method may comprise breaking organic cannabis buds into small pieces. Stems and sticks that are part of the plant may be removed as much as possible. This process may be performed manually or using any extraction device. If shake is being used, stems and sticks may be removed manually. Further, the weight of usable material may be weighed and recorded to calculate the resin yield at the end of the process. In one example, the plant material may be divided into two parts wherein ⅔ of the plant material may be decarboxylated and ⅓ will be retained in its acid bonded state.

This plant material (organic mixture) may be placed in food grade oven safe silicone container. The container may be sealed to reduce terpene loss. A convection or standard oven may be preheated around 240 to 250 degrees Fahrenheit and the container may be placed in the oven for 45 to 60 mins to decarboxylate. This approach allows most of the cannabinoids to decarb while retaining some in their original acid bonded state. THCA, CBD-A, and the like have higher anti-inflammatory properties than THC, CBD, and the like. Hence it may be important to retain THCA and CBDA to improve/retain the efficacy of the end-product which may be used for medicinal purposes.

Once decarboxylation is completed, the decarboxylated mixture along with the non-decarboxylated plant mixture may be mixed (this is optional and depends on the ratio of THC:THCA required by the user) and placed in a sealable container with enough high proof grain alcohol (95% ethanol) to cover the material. This intermediate mixture may be placed in a freezer for further processing. It is advised to provide pre-cooled alcohol (cooled at least for a period of 24 hrs) for preparing this intermediate mixture. This intermediate mixture may be placed in the freezer for around 2 hours. The intermediate mixture may be shaken every 10-20 minutes as well. The time required for processing this intermediate mixture may be dependent on the original source material and the size of the pieces (smaller pieces may get extracted in less time).

It is observed that this filtered mixture may have THC and THCA in the ratio of 2:1 based on the results of the lab tests done on preliminary samples. This points out that the abovementioned approach may yield a mixture/formula that contains both activated and inactivated THC, both of which have therapeutic value. This also provides insight into modifications of the process where the yield of THCA can be increased by withholding about ¼-⅓ of the plant material from the decarboxylation process. The approach may yield a formula that can provide therapeutic value to the medical cannabis patient. Further modifications of the process can be made where the yield of THCA can be increased by withholding varying amounts of the raw material from the decarboxylation process to approach a 1:1 ratio of THC-THCA.

Further, the processed mixture may be filtered using a filter and a press (such as a potato press) to generate a pure alcohol tincture with all the cellulose residue removed. Record weight of an empty crucible before proceeding to the next step. Further, for removing alcohol from this filtered mixture to form an extract, the filtered mixture may be placed in a solvent extractor such as a source turbo herbal extractor. The filtered mixture may be placed in a solvent extractor and the alcohol is removed using a combination of high vacuum pressure and low heat (up to 104 F). This method allows for about 98% of the alcohol to be reused this making this process more cost effective. This process may be repeated multiple times for the alcohol to be removed from the extract leaving behind the concentrated resin and this time varies based on the original volume of alcohol.

Once the alcohol extract has concentrated down such that bubbling activity has ceased extraction process may be stopped. The weight of the crucible with the extract may be recorded and used to determine the resin yield in grams as well as to calculate the resin percentage of the original raw material.

Furthermore, organic cold pressed extra virgin coconut oil is melted in a beaker in water bath and then added to crucible with the extract. This mixture may be stirred thoroughly. One tablespoon of organic lecithin liquid may be added for every 6 oz of organic cold pressed extra virgin coconut oil and stirring may be continued. This mixture may be poured into 24 oz mason or similar container and filled to 24 oz with organic cold pressed unrefined hemp seed oil and mixed again. Upon mixing, a normal strength Keira's Elixir is formed. This elixir may be sealed in a container and stored in a cool dark place.

The quantity of the contents that may be used in the abovementioned process to obtain about 24 fl. oz of the elixir may include approximately 2 oz of cannabis buds, approximately 18 fl. oz of organic cold pressed unrefined hempseed oil, approximately 6 fl. oz of cold pressed extra virgin coconut oil, approximately 1 table spoon of organic lecithin liquid, and at least 12 fl. oz of grain alcohol that is 190 proof and has at least 95% ethanol. To double the strength of the elixir, the quantity of the oils and lecithin may be reduced to half.

The elixir prepared using the techniques described above may be used topically, orally as a tincture, or in pill form. To make pills 000 capsule blanks may be used. The capsules may be pipetted with 1.3 ml into each capsule. This may be the starting dosage for individuals who may wish to take the medicine orally as it is a measured dose that can be consistently taken and increased as needed to achieve the desired level of relief.

The advantages of the techniques illustrated above include 1 providing a full spectrum cannabis extract. Known methods may not target or preserve terpenes of the cannabis flower unlike the present disclosure. This oil presents the active components of the cannabis from which it is made in the general proportion in which they are present in the plant. While some extracts may primarily focus on THC or CBD, or a combination of both (as these are the most prevalent cannabinoids in cannabis) they are not the only ones with potential positive health effects. Ingredients such as CBD-A, CBN, CBC, CBC-A, CBG, CBG-A, and the like offer potential health benefits. THC provides symptom relief while THCA can potentially reduce inflammation. Furthermore, the pills provided herein may not be mistaken for a candy and are also easily portable. This process may be scalable and can be configured to meet concentration requirements. For example, in Massachusetts, 5 mg of THC is a dose so in this market that would be the base dose per pill or per dropper of tincture. Furthermore, the end product may be used easily without providing extra calories or other side effects caused due to smoking or vaping of cannabis which could exacerbate health conditions. The elixir prepared using the abovementioned techniques may provide one or more of these ingredients thereby covering a range medicinal use case. Furthermore, the oil may be easily converted to pill forms that are easily portable and may also provide improved shelf life.

Examples described herein can also be used in various other scenarios and for various purposes. It may be noted that the above-described examples of the present solution are for the purpose of illustration only. Although the solution has been described in conjunction with a specific embodiment thereof, numerous modifications may be possible without materially departing from the teachings and advantages of the subject matter described herein. Other substitutions, modifications, and changes may be made without departing from the spirit of the present solution. All of the features disclosed in this specification (including any accompanying claims, abstract and drawings), and/or all of the steps of any method or process so disclosed, may be combined in any combination, except combinations where at least some of such features and/or steps are mutually exclusive.

The terms "include," "have," and variations thereof, as used herein, have the same meaning as the term "comprise" or an appropriate variation thereof. Furthermore, the term "based on," as used herein, means "based at least in part on." Thus, a feature that is described as based on some stimulus can be based on the stimulus or a combination of stimuli including the stimulus.

The present description has been shown and described with reference to the foregoing examples. It is understood, however, that other forms, details, and examples can be made without departing from the spirit and scope of the present subject matter that is defined in the following claims.

What is claimed is:

1. A method for preparing a full spectrum cannabis elixir, the method consisting essentially of:
   a) breaking cannabis buds into small pieces by removing the stems and the sticks of the cannabis to form a cannabis mixture;
   b) placing the cannabis mixture in an oven safe container;
   c) sealing the oven safe container and placing the oven safe container in an oven for approximately 45 minutes to 60 minutes with the temperature in the oven set between 240° F.- and 250° F. for decarboxylating the cannabis mixture;
   d) mixing the decarboxylated cannabis mixture with cold high proof grain alcohol to form an intermediate mixture in a sealable container;
   e) shaking the sealable container with a time gap of around 20 minutes to form a processed mixture;
   f) filtering the processed mixture using a press;
   g) removing alcohol from the filtered mixture to from an extract from the filtered mixture by placing the filtered material in a solvent extractor and subsequently placing the extract in a boiling water bath;
   h) melting organic cold pressed extra virgin coconut oil and mixing the melted oil with the extract in a crucible;
   i) stirring the contents in the crucible and adding organic lecithin liquid to form a mixture; adding organic cold pressed unrefined hemp seed oil to the mixture and mixing the contents to form the cannabis elixir; wherein 2 ounces of cannabis buds, 18 fluid ounces of organic cold pressed unrefined hempseed oil, 6 fluid ounce of cold pressed extra virgin coconut oil, 1 table spoon of organic lecithin liquid, and at least 12 fluid ounces of grain alcohol that is 190 proof and has at least 95% ethanol are used.

\* \* \* \* \*